United States Patent
Lidolt et al.

(10) Patent No.: US 11,179,261 B2
(45) Date of Patent: Nov. 23, 2021

(54) RELIEF ORTHOSIS

(71) Applicant: OTTO BOCK HEALTHCARE GMBH, Duderstadt (DE)

(72) Inventors: Klaus Lidolt, Duderstadt (DE); Boris Ljubimir, Bayreuth (DE); Matthias Vollbrecht, Herzberg (DE); Klaus Johannes, Gleichen (DE); Harry Christenhusz, Bad Bentheim (DE)

(73) Assignee: OTTOBOCK SE & CO. KGAA, Duderstadt (DE)

( * ) Notice: Subject to any disclaimer, the term of this patent is extended or adjusted under 35 U.S.C. 154(b) by 1071 days.

(21) Appl. No.: 14/784,686

(22) PCT Filed: Apr. 17, 2014

(86) PCT No.: PCT/EP2014/001035
§ 371 (c)(1),
(2) Date: Oct. 15, 2015

(87) PCT Pub. No.: WO2014/173512
PCT Pub. Date: Oct. 30, 2014

(65) Prior Publication Data
US 2016/0067077 A1 Mar. 10, 2016

(30) Foreign Application Priority Data

Apr. 22, 2013 (DE) .......................... 102013207256.2

(51) Int. Cl.
*A61F 5/01* (2006.01)
(52) U.S. Cl.
CPC .......... *A61F 5/0127* (2013.01); *A61F 5/0111* (2013.01)

(58) Field of Classification Search
CPC ...... A61F 5/0111; A61F 5/0127; A61F 5/014; A61F 5/14; A43B 7/142; A43B 7/143; A43B 17/02; A43B 17/023
See application file for complete search history.

(56) References Cited

U.S. PATENT DOCUMENTS

| | | | |
|---|---|---|---|
| 5,088,479 A | | 2/1992 | Detoro |
| 5,154,695 A | * | 10/1992 | Farris .................... A61F 5/0585 128/892 |
| 5,372,576 A | * | 12/1994 | Hicks .................... A61F 5/0111 128/882 |
| 5,421,822 A | | 6/1995 | Wang |
| 6,056,712 A | | 5/2000 | Grim |

(Continued)

FOREIGN PATENT DOCUMENTS

| | | |
|---|---|---|
| DE | 2744445 A1 | 4/1979 |
| DE | 9205681 U1 | 6/1992 |

(Continued)

OTHER PUBLICATIONS

PCT International Search Report for PCT International Patent Application No. PCT/EP2014/001035, dated Jul. 28, 2014.

*Primary Examiner* — Camtu T Nguyen
(74) *Attorney, Agent, or Firm* — Holland & Hart LLP (57) ABSTRACT

A relief orthosis includes a foot part which comprises a sole, a shank part extending away from the foot part in the proximal direction, and at least one fastening element for fastening the orthosis to a user, which fastening element is disposed on the foot part and/or on the shank part, and the foot part is embodied with an adaptable length.

21 Claims, 5 Drawing Sheets

(56) References Cited

U.S. PATENT DOCUMENTS

| | | | |
|---|---|---|---|
| 6,283,932 B1 | 9/2001 | Munch et al. | |
| 7,294,114 B1 * | 11/2007 | Clement | A61F 5/0111 36/15 |
| 7,666,155 B1 | 2/2010 | Jensen et al. | |
| 2008/0275451 A1 * | 11/2008 | McAllister | A61B 17/155 606/87 |
| 2011/0021963 A1 * | 1/2011 | Graddon | A61F 5/0127 602/27 |
| 2011/0099842 A1 * | 5/2011 | Burke | A43B 7/142 36/44 |
| 2014/0364782 A1 * | 12/2014 | Knecht | A61F 5/0123 602/16 |

FOREIGN PATENT DOCUMENTS

| | | |
|---|---|---|
| DE | 29924933 U1 | 12/2006 |
| EP | 0647440 A1 | 4/1995 |
| EP | 0955023 A1 | 11/1999 |
| EP | 1 234 560 1 * | 2/2002 |
| EP | 1 234 560 A1 * | 2/2002 |
| EP | 1 234 560 A1 * | 8/2002 |
| EP | 2 147 664 A1 * | 1/2010 |
| EP | 1 234 560 A1 * | 2/2020 |

\* cited by examiner

RELIEF ORTHOSIS

TECHNICAL FIELD

The invention relates to a relief orthosis with a foot part, which has a sole, with a shank part, which extends away from the foot part in the proximal direction, and with at least one fastening element, which secures the orthosis on a user and which is arranged on the foot part and/or on the shank part. A relief orthosis of this kind can be used in particular as a heel relief orthosis in calcaneal fractures.

BACKGROUND

Heel relief orthoses from the prior art are known, for example, in the form of the 28F10, which is sold by Otto Bock Healthcare GmbH and which permits early functional therapy of calcaneal fractures. The orthosis relieves the calcaneus and supports the longitudinal arch and the lower leg area. By means of exchangeable inserts, it is possible to exert greater weight successively on the calcaneus.

SUMMARY

The object of the present invention is to make available a relief orthosis with which it is possible to achieve improved individual adaptability to the patients.

According to the invention, this object is achieved by a relief orthosis having the features of the main claim. Advantageous embodiments of the invention are disclosed in the dependent claims, the description and the figures.

In the relief orthosis with a foot part, which has a sole, with a shank part, which extends away from the foot part in the proximal direction, and with at least one fastening element, which secures the orthosis on a user and which is arranged on the foot part and/or on the shank part, provision is made that the foot part is designed to be modifiable in length. The adjustability of the length of the foot part permits exact adaptation of the orthosis to the length or width of the foot and thus to the respective patients, without a separate orthosis having to be produced for each foot size or without a patient having to wear an orthosis that is not an exact fit.

In a development of the invention, a longitudinal arch preform is provided, which is secured on the foot part and which relieves a calcaneus during walking or standing. In the case of a calcaneal fracture, the longitudinal arch preform makes it possible for the calcaneus to be initially relieved completely of any stress, and for the forces that occur to be carried off via the plantar arch, the sole and the shank part, such that, particularly after fresh fractures, no load or only a very slight load can initially be exerted on the calcaneus.

The foot part can be of a multi-part design and have a forefoot component and a heel component, which are designed to be movable relative to each other and to be able to be secured on each other. It is thereby possible that the forefoot component is movable relative to the heel component and can be fixed in the respectively desired mutual position. Provision is also made that the length in the transverse direction is also modifiable, such that the width of the relief orthosis can be adjusted.

The forefoot component and the heel component can be mounted on each other in a longitudinal guide, for example in a rail and groove guide, and can be fixed to each other via clamping elements or form-fit elements. It is thereby possible, by simply releasing or removing the clamping elements or form-fit elements, to produce the longitudinal displaceability of the two foot part components in relation to one another and, after the positioning of the components relative to each other, to lock them in the desired setting. The longitudinal guide makes the displacement in this case easier, since a basic assignment and orientation of the forefoot component to the heel component is maintained.

Latching elements can be arranged or formed in or on the forefoot component and the heel component in order to orient the two components relative to each other. It is likewise possible that orientation markings are present on the forefoot component and/or on the heel component and make it possible to orient the components relative to each other, to adjust the length of the orthosis and then to fix the latter by means of clamping elements, form-fit elements or other devices.

For their part, the fastening elements with which the orthosis can be secured on the user can be secured movably on the foot part and/or on the shank part, such that the individualization of the orthosis can be further improved, since the fastening elements are positioned at those locations on the orthosis where the orthosis can be secured in the best possible way while at the same time ensuring the least possible impediment and the maximum level of comfort for the person using the orthosis.

The fastening elements can be secured on oblong holes or in recesses or holding devices arranged at discrete from one another. The recesses or holding devices secure the area along which the fastening elements can be secured on the foot part and/or shank part. Oblong holes permit a stepless displacement of the fastening elements and, therefore, an autoadaptive orientation for the respective user.

The longitudinal arch preform can be secured releasably or movably on the foot part, for example by hook-and-loop fastener connections, a longitudinal guide or bores or threads arranged at distances from each other, such that securing can be achieved at discrete distances or in a manner movable almost continuously.

The hook-and-loop fastener elements can be designed to be able to be secured in several positions on the foot part, wherein the hook-and-loop fastener elements are in particular provided to secure the longitudinal arch preform on the foot part. For this purpose, provision is made that the hook-and-loop fastener elements form part of the hook and loop components of a hook-and-loop fastener, such that the longitudinal arch preform can be secured on the foot part in a manner tailored to the individual user.

The fastening elements for securing the orthosis on the foot can be designed as a Y-shaped hook-and-loop connection, so as to be able to achieve an easily adaptable length. The Y-shaped hook-and-loop element is advantageously formed as hook elements on a surface and the mutually opposite inner faces, while the rest of the fastening element is designed as a fleeced element, such that, by shortening the fleeced element and securing the Y-shaped hook-and-loop element on the fleeced element, it is possible to achieve a length adaptability. To secure the orthosis on the foot or shank, the fastening element can be guided through a slit or a deflection element and can be folded back and fixed on itself.

Markings for shoe sizes can be provided on the outer face of the foot part, either on the forefoot component or on the heel component, such that a rough initial setting can be made on the basis of the fundamentally known size of the person using the orthosis. Likewise, markings can be provided on the foot part for positioning the longitudinal arch preform according to the usual shoe sizes, so as to permit an initial setting and easier positioning of the longitudinal arch preform.

Advantageously, the relief orthosis with the foot part and the shank part is designed symmetrically in the longitudinal direction, such that it can be used both on the right foot and on the left foot. The heel component then serves as a so-called container which encloses the heel in four directions. An X-ray point can be arranged in or on the shaped longitudinal arch part, so as to be able to carry out the physiologically exact positioning of the longitudinal arch preform inside the relief orthosis. After the orthosis has been put on for the first time, the X-ray point, which has a relatively high density and can be made of metal for example, allows an X-ray to be taken to check whether the longitudinal arch preform is correctly positioned.

BRIEF DESCRIPTION OF THE DRAWINGS

Illustrative embodiments of the present invention are explained in more detail below with reference to the attached figures, in which.

DETAILED DESCRIPTION

Figure 1:
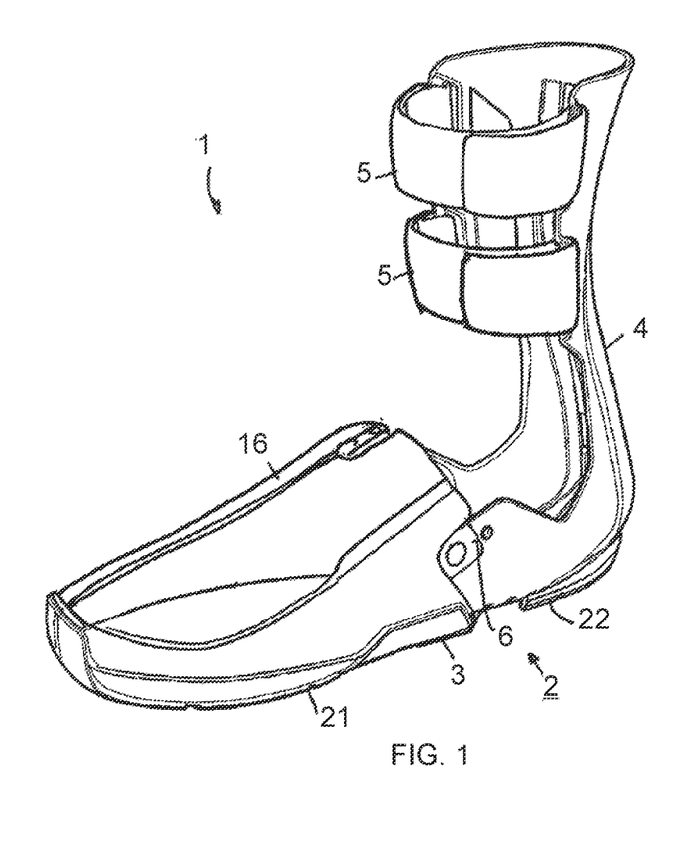
FIG. 1 shows a perspective overall view of a relief orthosis.

FIG. 1 shows a relief orthosis 1 in the form of a heel relief orthosis with a foot part 2, which has a sole 3. The sole 3 is adjoined, at the rear end, by a shank part 4, which extends from the foot part 2 in the proximal direction. Fastening elements 5, 6 are arranged both on the foot part 2 and also on the heel part 4 in order to fit the relief orthosis 1 on a user (not shown). The fastening elements 5 on the heel part 4 are in the form of hook-and-loop fastener straps. The fastening elements 5 provide for the anterior closure of the heel part 4, which is closed in the posterior direction.

A fastening element 6 extending across the instep and in the form of a hook-and-loop fastener strap is secured on the foot part 2. After they have been guided through a guide, a D-ring, a tab or a slit, the fastening elements 5, 6 on the heel part 4 and on the foot part 2 are folded back on themselves and secured in order to fasten the relief orthosis 1 on the foot.

The foot part 2 with the sole 3 is designed in two parts and has a forefoot component 21 and a heel component 22. The forefoot component 21 is secured movably on the heel component 22. From the heel component 22, the shank part 4 extends integrally in the proximal direction. In addition to the shank part 4 being designed integrally with the heel component 22, it is possible to design the shank part 4 and the heel component 22 as separate components that are secured on each other.

A protective cover 16 is arranged on the forefoot component 21 and is designed to be able to be closed so as to surround the foot and give a shoe-like appearance when the relief orthosis is fitted.

Figure 2:
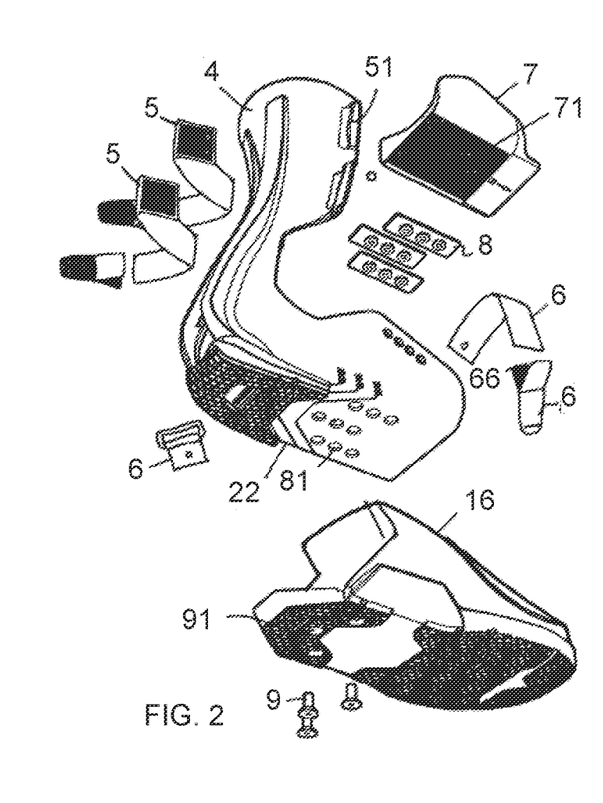
FIG. 2 shows an exploded view of a first embodiment.

FIG. 2 shows a first variant of the relief orthosis 1 in an exploded view seen obliquely from below. The individual elements of the relief orthosis 1 are shown. In addition to the integral design of the heel component 22 with the shank part 4, the fastening elements 5, 6 are shown in the form of a Y-shaped hook-and-loop fastener. The fastening elements 5 on the shank part 4 are guided through oblong holes 51 which are arranged medially and laterally on the proximal end of the shank part 4. With the aid of the oblong holes 51, it is possible, on the one hand, to achieve mobility in the proximal-distal direction and, on the other hand, to guide the free end of the fastening element 5 through the hole, fold it back on itself and secure it to itself. For this purpose, provision is made that a part of the fastening element 5 is designed as a fleeced strap, at the end of which a Y-shaped piece is arranged which has hook components on at least one side such that, after the Y-shaped piece has been guided through an oblong hole 51 and has been folded back onto the fleeced strap, it can be secured on the latter.

Recesses 61 are arranged next to each other on the heel component 22 and extend in the anterior-posterior direction, such that the fastening element 6, which is likewise designed as a Y-shaped hook-and-loop strap, can be secured at the respectively desired position. A D-shaped buckle, provided as a mating piece, can be arranged on a corresponding recess 61 on the upper edge of the shell-like part of the heel component 22.

In the illustrative embodiment shown, three holes 81 oriented in the anterior-posterior direction are formed in three rows arranged alongside each other on the sole area of the heel component 22 and are intended to receive corresponding projections in hook-and-loop fastener elements 8. Threads are formed in the projections on the hook-and-loop fastener elements 8 in order to screw in screws 9 through recesses 91 and through the holes 81 and thus secure the forefoot component 21 in one of the three possible positions. Markings 25 arranged on the outer face of the heel component 22 or marking 72 of the forefoot component 21 (see FIG. 3) indicate the size setting in which the forefoot component 21 is secured on the heel component 22.

On the top face directed toward the user, the hook-and-loop fastener element 8 is provided respectively with the loops or hooks of a hook-and-loop fastener 82 in order to cooperate with the corresponding hook-and-loop fastener element 71 arranged on the underside of a longitudinal arch preform 7. The longitudinal arch preform 7 can be placed in the desired position in the anterior-posterior direction onto the hook-and-loop fastener elements 8 and fixed in position. It is thus possible for the longitudinal arch preform 7 to be assigned to the shank part 4, the heel component 22 and the forefoot component 21 in a way which, although modifiable, is set in the chosen position.

Figure 3:
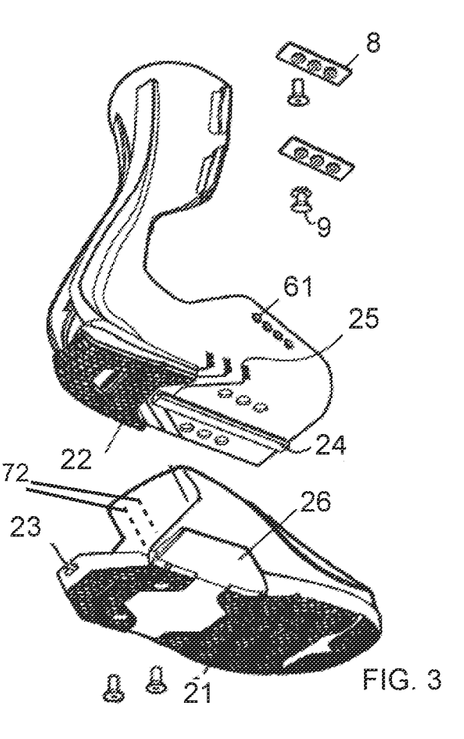
FIG. 3 shows an exploded view of a second embodiment.

FIG. 3 shows, in the same perspective as in FIG. 2, a variant of the invention in which, instead of three hook-and-loop fastener elements 8, there are only two. A guide rail 24 with a T-shaped cross section is arranged on the underside of the heel component 22. A corresponding groove 23 is worked into the top face of the forefoot component 21, such that the forefoot component 21 is movable in the anterior-posterior direction along a longitudinal guide which is formed by the T-shaped rail 24 and the corresponding groove 23. With the aid of the screws 9, the forefoot component 21 can be secured on the heel component 22 either with a form fit or by clamping. Other fixing options are also possible. A size adjustment can be carried out using the markings 25, the orientation of the forefoot component 21 with respect to the heel component 22 determining whether the markings 25 are concealed by a flap 26 (which may also act as an orientation marking) or exposed.

Figure 4:
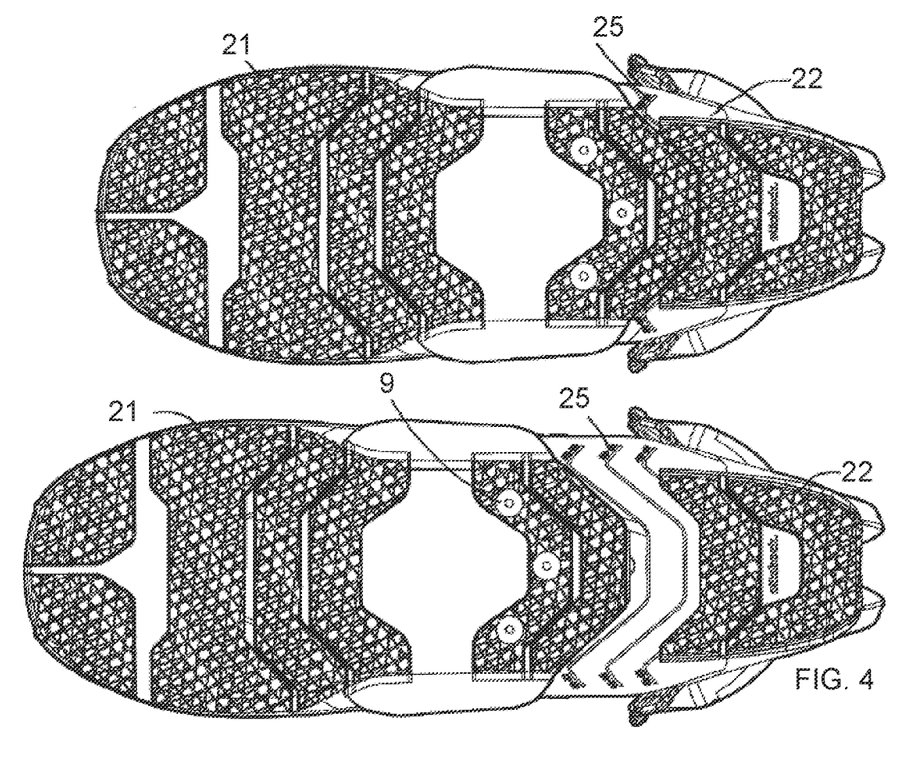
FIG. 4 shows bottom views of a relief orthosis in different lengths.

FIG. 4 shows a relief orthosis 1 in a bottom view in different length settings. The upper view shows the forefoot component 21 and the heel component 22 in the position in which they are as close as possible to each other, i.e. in the shortest version of the relief orthosis 1. Only one marking 25 can be seen. In the view underneath, the screws 9 are screwed into the front threads of the hook-and-loop fastener elements 8, such that three markings 25 can be seen, which means that the longest version of the relief orthosis 1 has been set.

Figure 5:
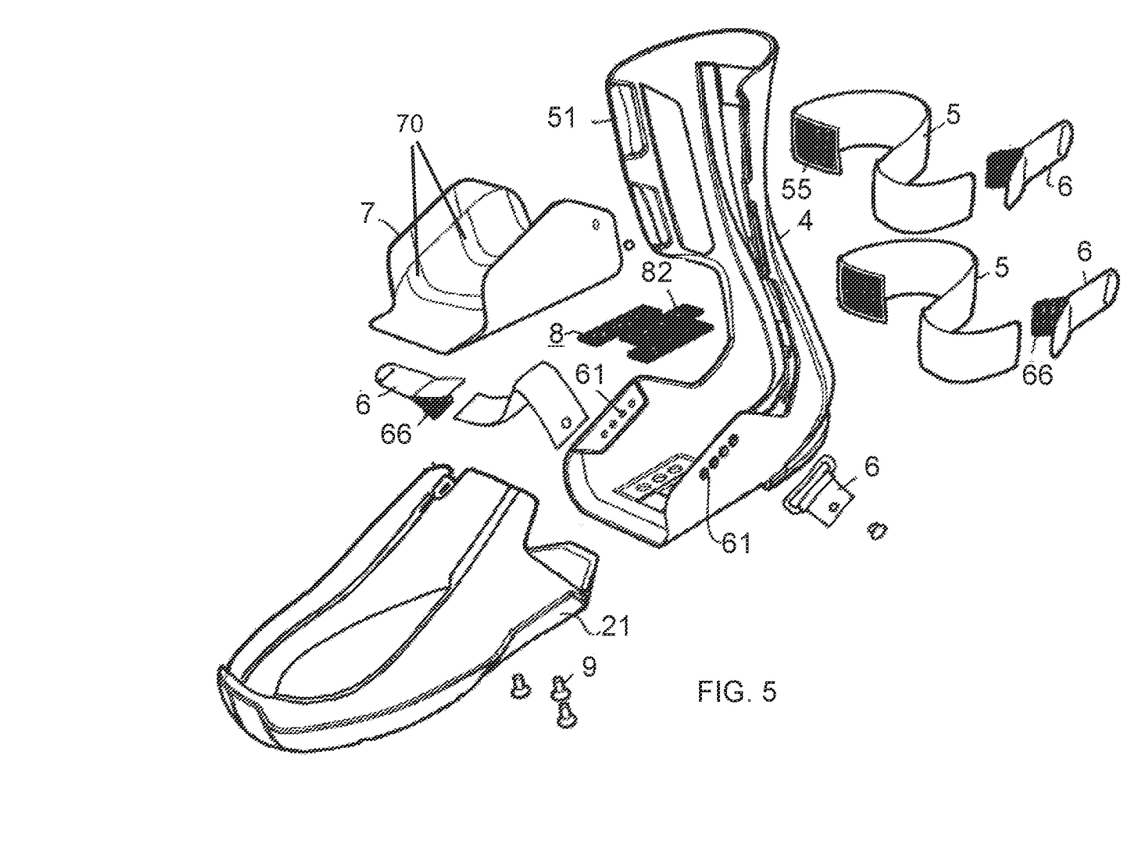
FIG. 5 shows an exploded view of the variant from FIG. 2 seen obliquely from above.

In FIG. 5, the relief orthosis 1 according to FIGS. 1 and 2 is shown in another perspective view. The individual components correspond to those of FIGS. 1 and 2, except that the oblong holes 51 and the designs of the fastening elements 5, 6 as Y-shaped hook-and-loop fastener tapes can be better seen. Similarly, the hook-and-loop fastener elements 8 with the hook or loop elements on the top face for adjustable securing of the longitudinal arch preform 7 on the orthosis can be better seen. Through the recesses in the fastening elements 6 across the instep, a form-fit securing on the holes 61 in the heel component 21 can be obtained via stoppers, screws or the like.

Profile elements can be mounted on the underside of the foot part 2 in order to provide an improved hold on the ground. The forefoot component 21 can be flexurally elastic in order to permit rollover.

As noted above, one or more X-ray points 70 (see FIG. 5) can be arranged in or on the shaped longitudinal arch part 7, so as to be able to carry out the physiologically exact positioning of the longitudinal arch preform 7 inside the relief orthosis. After the orthosis has been put on for the first time, the X-ray points 70, which have a relatively high density and can be made of metal for example, allows an X-ray to be taken to check whether the longitudinal arch preform 7 is correctly positioned.

Figure 6:
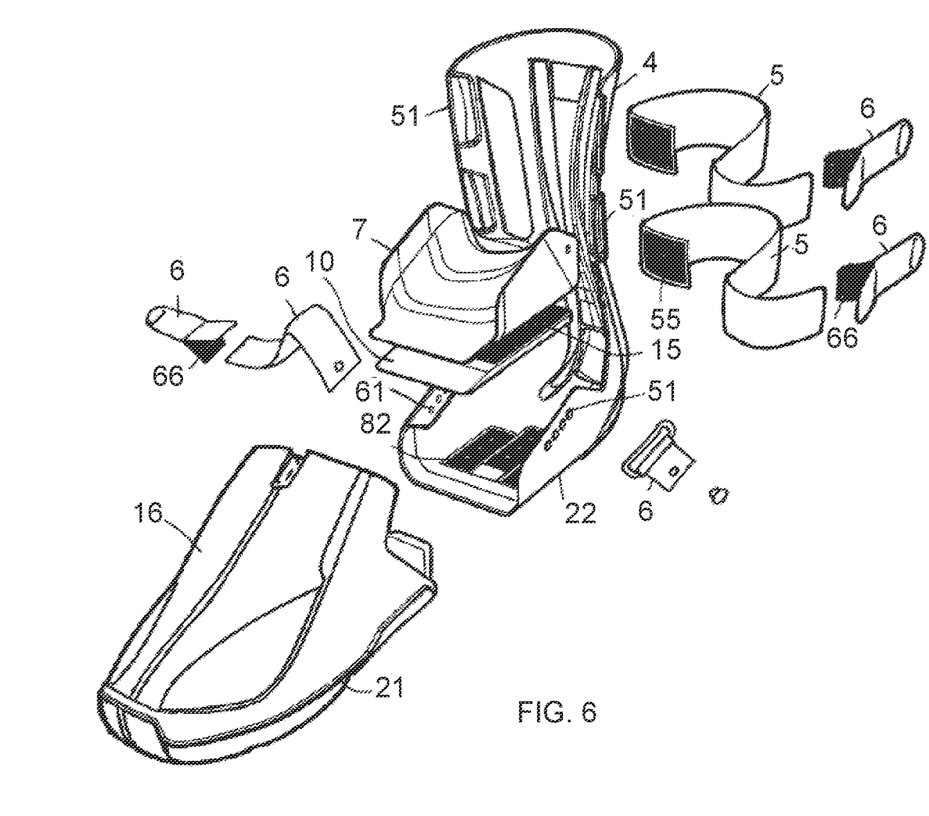
FIG. 6 shows a perspective view of a further variant.

FIG. 6 shows a variant of the invention in which, instead of the longitudinal arch preform 7 being secured directly on the hook-and-loop fastener 82 of the hook-and-loop fastener elements 8, an intermediate piece 10 is provided which, on the top face, is provided with a hook-and-loop fastener area 15, which is designed correspondingly to the hook-and-loop fastener 82 of the hook-and-loop fastener elements 8, such that the longitudinal arch preform 7 can be held securely on the intermediate piece 10. On the underside of the intermediate piece 10, a hook-and-loop fastener element (not visible) is arranged which corresponds to the underside of the longitudinal arch preform 7 in order to permit fixing of the intermediate piece 10 on the hook-and-loop fastener elements 82 in the heel component.

FIG. 6 also shows in more detail that the fastening elements 5 can have hook areas 55 in order to permit fixing on the relief orthosis via the remaining fleeced area of the fastening tapes. It will also be seen that the Y-shaped hook-and-loop fastener tapes 6 are provided with hook areas 66 for placing on fleeced portions of the fastening elements 5, 6. This embodiment with the hook areas 66, 55 can likewise be designed in all illustrative embodiments of the aforementioned figures.

The invention claimed is:

1. A relief orthosis for use during walking or standing, comprising:
   a foot part, which has a sole, a heel component and a forefoot component, the forefoot component being flexurally elastic, the heel component and forefoot component each defining portions of the sole;
   a shank part, which extends away from the foot part in a proximal direction;
   at least one fastening element configured to secure the relief orthosis on a user and which is arranged on at least one of the foot part and the shank part;
   a longitudinal arch preform secured on the foot part and configured to provide complete relief of a calcaneus of the user during walking or standing, the longitudinal arch preform including an X-ray orientation point arranged in or on the longitudinal arch preform, wherein the X-ray orientation point comprises a metal insert;
   wherein the longitudinal arch preform is configured to extend across an entire width of the foot part;
   wherein the foot part is designed to be modifiable in length by adjusting a position of the forefoot component relative to the heel component.

2. The relief orthosis as claimed in claim 1, wherein the forefoot component and the heel component are designed to be movable relative to each other and to be able to be secured on each other.

3. The relief orthosis as claimed in claim 2, wherein the forefoot component and the heel component are mounted on each other in a longitudinal guide and can be fixed to each other via clamping elements or form-fit elements.

4. The relief orthosis as claimed in claim 2, wherein the forefoot component and the heel component have at least one orientation marking, in order to orient the components with respect to each other.

5. The relief orthosis as claimed in claim 1, wherein the at least one fastening element is secured movably on at least one of the foot part and the shank part.

6. The relief orthosis as claimed in claim 1, wherein the at least one fastening element is secured on oblong holes or in recesses arranged at discrete distances from one another.

7. The relief orthosis as claimed in claim 1, further comprising hook-and-loop fastener elements configured to be secured in several positions on the foot part.

8. The relief orthosis as claimed in claim 1, wherein the longitudinal arch support has a shell-like construction that is configured to raise a metatarsal area of the foot.

9. The relief orthosis as claimed in claim 1, wherein the longitudinal arch preform is secured releasably or movably on the foot part.

10. The relief orthosis as claimed in claim 1, wherein the longitudinal arch preform is secured on the foot part via at least one hook-and-loop fastener connection, a longitudinal guide or bores or threads arranged at distances from one another.

11. The relief orthosis as claimed in claim 10, wherein the longitudinal guide comprises a guide rail having a T-shaped cross section.

12. The relief orthosis as claimed in claim 1, wherein the at least one fastening element is designed as a Y-shaped hook-and-loop tape.

13. The relief orthosis as claimed in claim 12, wherein the heel component defines a plurality of recesses arranged at discrete distances from one another, wherein the at least one Y-shaped hook-and-loop tape is secured to at least one of the recesses.

14. The relief orthosis as claimed in claim 1, wherein the relief orthosis is designed as a heel relief orthosis.

15. A relief orthosis for use during walking or standing, comprising:
   a foot part having a sole, a forefoot component, a heel component, and an adjustable length, the forefoot component being flexurally elastic, and the forefoot component and heel component each defining portions of the sole;

a shank part extending away from the foot part in a proximal direction;

at least one fastening element configured to releasably connect the relief orthosis to a user, the at least one fastening element being arranged on one of the foot part and the shank part;

a longitudinal arch preform secured on the foot part and configured to provide complete relief of a calcaneus of the user during walking or standing, the longitudinal arch preform including an X-ray orientation point arranged in or on the longitudinal arch preform, wherein the X-ray orientation point comprises a metal insert, and wherein the longitudinal arch preform is configured to extend across an entire width of the foot part.

16. The relief orthosis as claimed in claim 15, wherein the forefoot component and the heel component are configured to move relative to each other and be connected to each other.

17. The relief orthosis as claimed in claim 16, further comprising a longitudinal guide, wherein the forefoot component and the heel component are connected to each other in the longitudinal guide and can be fixed to each other via clamping elements or form-fit elements.

18. The relief orthosis as claimed in claim 16, wherein the forefoot component and the heel component include orientation markings to orient the forefoot and heel components with respect to each other.

19. The relief orthosis as claimed in claim 15, wherein the at least one fastening element is adjustably connected to at least one of the foot part and the shank part.

20. The relief orthosis as claimed in claim 15, wherein the at least one fastening element is connected to spaced apart oblong holes or recesses.

21. A relief orthosis to provide relief to a user during walking or standing, comprising:

a foot part having a sole, a forefoot component, a heel component, and an adjustable length, the forefoot component and heel component each defining portions of the sole;

a shank part, which extends away from the foot part in a proximal direction;

at least one fastening element, which is configured to secure the relief orthosis on a user and which is arranged on at least one of the foot part and the shank part;

a longitudinal arch preform secured on the foot part and configured to provide complete relief of a calcaneus of the user during walking or standing, the longitudinal arch preform including an X-ray orientation point arranged in or on the longitudinal arch preform, wherein the X-ray orientation point comprises a metal insert, and wherein the longitudinal arch preform is configured to extend across an entire width of the foot part.

* * * * *